United States Patent [19]
Mills

[11] Patent Number: 4,815,448
[45] Date of Patent: Mar. 28, 1989

[54] MOSSBAUER CANCER THERAPY

[76] Inventor: Randell L. Mills, R.D. 2, Cochranville, Pa. 19330

[21] Appl. No.: 849,046

[22] Filed: Apr. 7, 1986

Related U.S. Application Data

[63] Continuation-in-part of Ser. No. 713,448, Mar. 19, 1985.

[51] Int. Cl.$^4$ ............................................. A61N 5/12
[52] U.S. Cl. ..................................... 600/2; 128/654; 378/3; 378/65
[58] Field of Search .................. 250/83.3 R; 128/1.1, 128/1.3, 654, 653; 424/9; 378/3, 65

[56] References Cited

U.S. PATENT DOCUMENTS

| | | | |
|---|---|---|---|
| 3,257,558 | 6/1966 | Cook et al. | 250/83.3 |
| 3,631,247 | 12/1971 | Barton, Jr. | 250/83.3 R |
| 3,794,840 | 2/1974 | Scott | 250/363 |
| 3,872,333 | 3/1975 | Imbert et al. | 378/3 |
| 4,361,544 | 11/1982 | Goldenberg | 424/9 |
| 4,516,535 | 5/1985 | Russell, Jr. et al. | 128/1.1 |
| 4,541,438 | 9/1985 | Parker et al. | 128/654 |

FOREIGN PATENT DOCUMENTS

| | | |
|---|---|---|
| 0198257 | 10/1986 | European Pat. Off. |
| WO85/01871 | 5/1985 | World Int. Prop. O. |

OTHER PUBLICATIONS

2389 Medical Physics, vol. 12, No. 4 Jul./Aug. 1985, pp. 532–536, New York, "Photon Activation Therapy", Fairchild et al.

Nuclear Instruments and Methods, vol. 155, No. 1/2, Sep. 1978, pp. 97–101, North Holland Publishing Co., "High Field Mossbauer Spectrometer Using Bitter Magnets".

8164 Instruments and Experimental Techniques, vol. 24, No. 5, part 1, Sep./Oct. 1981, pp. 1151–1153, Plenum Publishing Corp., New York, U.S.S. M. Irkaev et al, "Isomer-Shift Compensation with Resonance Detectors in Mossbauer Spectroscopy".

2107B Nuclear Instruments & Methods, section B14, No. 3, Mar. 1986, pp. 323–340, Elsevier Science Publishers B.V., Holland, J. G. Mullen et al. "Cold Moving Mice: a Microfoil Internal Conversion Electron Detector for Low and Intermediate Energy Mossbauer Transitions".

*Primary Examiner*—C. Fred Rosenbaum
*Assistant Examiner*—Mark F. Colosimo
*Attorney, Agent, or Firm*—Weingarten, Schurgin, Gagnebin & Hayes

[57] ABSTRACT

Frequency selective radiation therapy providing selective tissue damage or necrosis by irradiating a component element of the target tissue at the corresponding Mossbauer absorption frequency. The component radiation absorption at the Mossbauer absorption frequency is thus enhanced many times over the absorption of the surrounding tissue having a different Mossbauer absorption frequency. The energy thusly absorbed by the target tissue component is converted to and remitted as Auger electrons, which provide intranuclear radiation resulting in lethal double strand breaks in the DNA molecules of the target tissue. The therapy is administered in frequency and tissue selective modes of treatment, and may be combined with conventional chemotherapeutic agents to provide a further enhanced treatment modality. Moreover, the source frequency can be adjusted to enhance the killing effect. The therapy method and apparatus according to the present invention is useful in combination with naturally occurring or administered pharmaceutical stable isotope absorbers, having significantly reduced side effects by comparison to conventional chemotherapy or radiation therapy.

38 Claims, 2 Drawing Sheets

MOSSBAUER CANCER THERAPY

CROSS REFERENCE TO RELATED APPLICATIONS

This application is a continuation-in-part of my copending application Ser. No. 713,448, filed Mar. 19, 1985.

FIELD OF THE INVENTION

The present invention relates to therapeutic methods and apparatus, and specifically to frequency selective radiation therapy for cancer.

BACKGROUND OF THE INVENTION

In the treatment of tumors by ionizing radiation, x-rays or gamma rays are particularly used. The ideal in radiation therapy of malignant disease is achieved when the tumor is completely eradicated and the surrounding normal tissue, in the treated volume, show little or no evidence of structural or functional injury. The important factor in successful treatment is the difference in radiosensitivity of neoplastic and normal cells. All tissues, normal and neoplastic, are effected by radiation so that radiosensitivity is a relative term. The basis of radiation therapy is that cells that are actively proliferating or that are of a primitive type are more sensitive than normal tissue so that there is usually a considerable margin between doses that are damaging to neoplastic and to normal cells. The difference depends on the capacity for intracellular repair of normal and neoplastic cells and the ability of normal organs to continue to function well if they are only segmentally damaged. If surrounding tissue can tolerate twice the radiation dose of a given tumor, then the tumor is radiosensitive.

Mammalian cells are capable of accumulation radiation damage before they are killed exponentially. Also, if allowed sufficient time after exposure, mammalian cells are capable repairing sublethal and potentially lethal radiation damage. The effects of x-rays or gamma rays on growing cells vary with intensity and duration of exposure and consist of destruction of some cells, inhibition of imminent mitosis; followed by abnormal mitosis and disruption of the cells and damage to resting cells so that continued proliferation fails. The prime target of present radiotherapy is the DNA molecule of a cell which does not select for cancer cells but selects for DNA repair capabilities. Even a two-to-one increase in radiation sensitivity in cancer cells will result in a curable condition. However, normal surrounding tissue may not be more tolerant to x-ray therapy than cancer tissue which makes this therapeutic modality useless.

SUMMARY OF THE INVENTION

Mossbauer absorption, which is the resonant absorption of gamma rays by nuclei, represents a method of increasing the radiosensitivity of tumors in terms of orders of magnitude via selective energy deposition in cancer cells. Mossbauer radiation is completely analogous to optical absorption. In the latter, the ultimate source of radiation consists of excited atoms or molecules which decay to the ground state. The radiation after being suitably monochromatized by a prism or diffraction grating is incident upon the sample and the intensity of the beam which is transmitted through the sample (absorber) varies as a function of the frequency as photons of energy equivalent to electronic, vibrational, rotational, and translational transitions are absorbed. In Mossbauer absorption, the source comprises excited nuclei which in decaying to their ground state emit gamma radiation with certain nuclei in appropriate surroundings, such as exist in a crystal lattice, the radiation is highly monochromatic. In fact, the gamma ray line can be so narrow that its frequency may be shifted significantly by incorporating the source or absorber in a mass driver oscillating at moderate velocities to produce a Doppler effect. The velocity of the mass driver which provides a Doppler shift to the gamma ray photons functions analogously to the dispersion device in optical absorption. By varying the driving velocity, a resonance system can be driven by the emitted gamma photons and the nuclear energy transitions of the sample (absorber). The absorber may occur naturally, or as in the preferred embodiment, comprise added stable pharmaceutical isotopes, discussed below.

Furthermore, since it has been determined that cancer cells differ from normal cells with respect to level of aerobic versus anaerobic metabolism, internal concentrations of ions such as $Ca^{2+}$ and $Mg^{2+}$, pH, spin lattice relaxation times, and resting membrane potentials, it is believed that such differences would cause differences in the nuclear microenvironment in cancer cells versus normal cells significant enough to result in excitation energy differences on the order of $10^{-6}$ eV. Such excitation differences will affect Mossbauer absorption, and would allow for selective targeting of cancer cells. Thus, exposing malignant tissue with, for example, an Fe-57 absorber pharmaceutical to a narrow line width beam of 14.4 KeV photons having a photon energy equal to the Fe-57 nuclear transition of pharmaceutical (in this tissue), which is different from normal tissue transition and therefore represents a powerful treatment modality.

BRIEF DESCRIPTION OF THE DRAWING

These and other features of the present invention will be further understood by reading the following detailed description, taken in combination with the drawing, wherein.

DETAILED DESCRIPTION OF THE INVENTION

Figure 1:
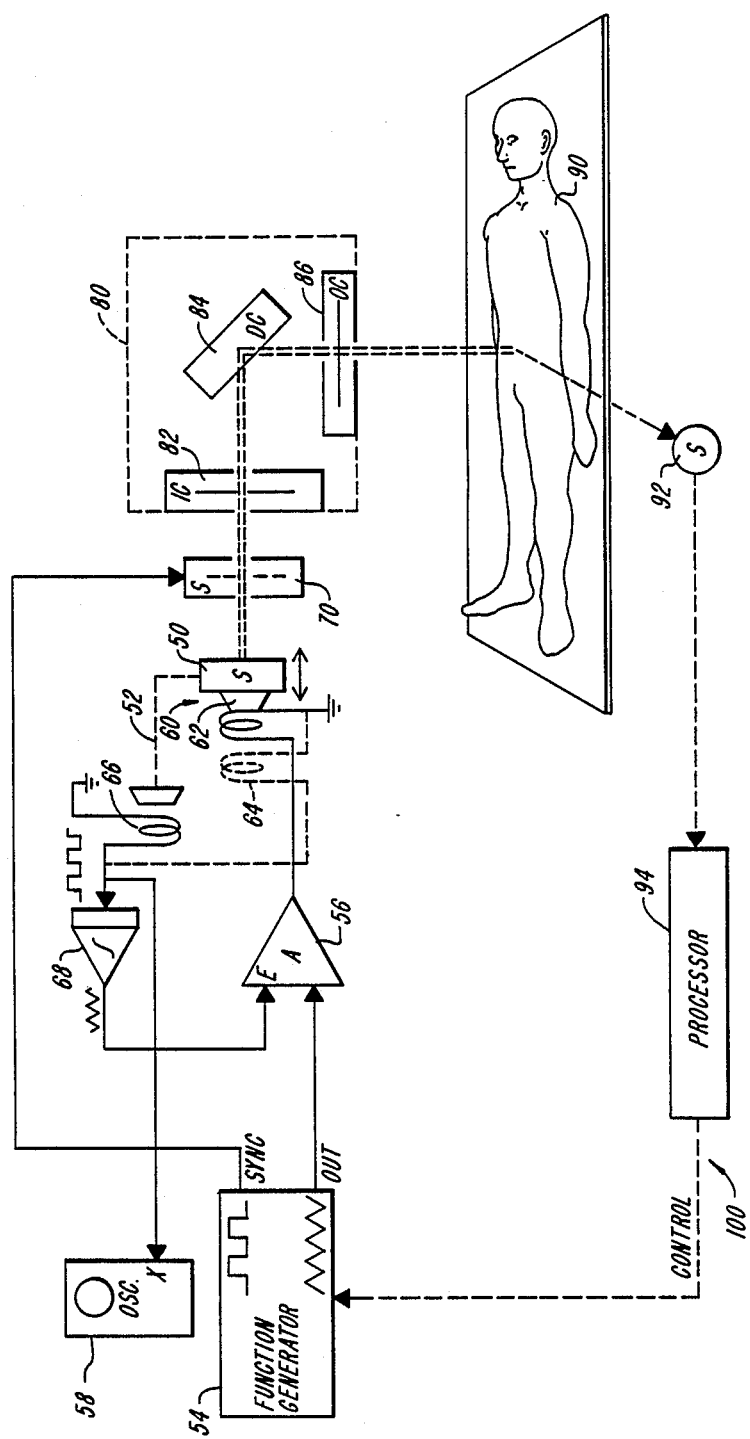
FIG. 1 is one embodiment of the apparatus according to the present invention.

The most dramatic killing effect of radiation has been shown to be due to intranuclear radiation effects of internal conversion and Auger electrons which result in lethal double stranded breaks in DNA molecules. (Commerford et al. 1980 and Linz et al. 1983). Internal conversion results in the ejection of inner shell electrons. The difference between the ionization energy of the inner shell electron and that of the outer shell is released either in the form of fluorescence x-ray photon or is transmitted to another electron which is then ejected as an Auger electron. The process continues, shell by shell, until the valence shell is reached and thus leads to multiple ionizations of the atom. Such a valency cascade is known as the Auger effect. For elements of low or medium atomic number, the Auger electrons have energies to a few KeV with a relatively high linear energy transfer (LET) of 1 to 10 ev/nm. Since such electrons dissipate their energy in materials of unit density within a distance of the order of 10 to 100 nm, they may efficiently damage molecules in the nearness of the decay event.

Mossbauer absorption depends on the microelectronic environment of the nucleus. The energy of the nuclear transitions of the absorber is dependent on the S electron density, electric field gradient, and effective magnetic field at the position of the nucleus in which resonant gamma ray absorption occurs. Therefore, absorption is affected by the bonding in the Mossbauer nucleus-drug complex and factors which affect this bonding such as pH, ionic strength, ionic charge of the central atom, concentration of ions such as $Mg^{+2}$ and $Ca^{+2}$ as well as electric and magnetic fields.

Mossbauer nuclei absorb gamma radiation and are excited to a high energy nuclear state. Following recoilless absorption, the predominant mode of decay is by internal conversion. For example, following resonant absorption of the incident gamma ray the excited $^{119}Sn$ nuclei in the absorber undergo internal conversion 84 percent of the time. In a paper by Yagnik et al. (1974), 84,20 KeV internal conversion and 75,3 KeV Auger electrons are re-emitted for every 100 gamma rays resonantly absorbed. Approximately half of these electrons are emitted in the backward direction, which is not the case with particle radiation. The remainder of excited nuclei re-emit gamma or x-rays. Thus, Mossbauer cancer therapy promises the advantages of selective radionucleotides without systemic radiation of normal tissue, higher kill per event secondary to production of Auger electrons, and higher kill per atom due to the fact that once a Mossbauer absorber atom decays it will be re-excited with probability equal to the original excitation event.

Momentum and energy are conserved during an emission event. For a free atom of mass M the recoil energy due to emission of a photon of energy Eo is $Eo^2/2Mc^2$, where c is the velocity of light. If the atom is in motion during emission, the photon energy will be modified by a term $E/(V/c)/\cos\sigma$, where V is the velocity of the atom and $\sigma$ is the angle between V and the momentum vector of the photon. The energy of the photons emitted by such atoms is given by (emission)

$$E = Eo - Eo^2/2Mc^2 + Eo(V/c)/\cos\sigma \quad (1)$$

where Eo is the photon energy in the rest frame of the nucleus. The photon energy for resonant absorption by a similar nucleus moving with velocity V' and direction $\sigma'$ is (absorption):

$$E' = Eo + Eo^2/2Mc^2 + Ec(V'/c)\cos\sigma \quad (2)$$

The energy of gamma rays emitted by a system of free atoms moving with thermal velocities would be centered at $Eo - Eo^2/2Mc^2$ while the resonant absorption cross-section would be centered at $Eo + Eo^2/2Mc^2$. Thus, resonant absorption would be expected to occur for the fraction of events represented by the overlap in energy of the emission and absorption lines. The width of this overlap region is of the order of thermal energy: about $10^{-2}$ eV at room temperature. If the atom is in a bound state, a deviation from Equations 1 and 2 is observed. Mossbauer discovered that a certain fraction of gamma rays emitted by Ir-91 nuclei in a solid do not obey Equation 1; instead, they had energy equal to Eo and a line width $\Theta = \hbar/Tm$, where Tm is the mean life of the excited state, corresponding effects were observed in absorption. The significant fact is that the emitting (or absorbing) atom is bound to other atoms in a solid. There then exists a certain probability that the recoil momentum associated with the emission (or absorption) of a photon will be taken up by the lattice rather than by the individual atom. When this occurs, the recoil energy $Eo^2/2Mc^2$ becomes vanishingly small because M is now essentially the mass of the crystal rather than the mass of a single atom. In addition, the lattice has a discrete set of vibrational transitions. This means that the last term in Equation 1 or 2 is replaced by a quantity which describes the number of photons that have been interchanged between the lattice and the gamma ray photons. There is a nonvanishing probability that no photons are exchanged. When these conditions prevail, the emission (or absorption) is described as "recoilless" or "recoil-free," and emitted (or absorbed) photons match very closely the energy and level widths of the nuclear transition. This feature characterizes the Mossbauer effect, which is applied for therapeutic treatment according to the present invention.

The probability of a recoilless event (emission or absorption) depends on certain properties of the solid as well as the energy and mean life of the nuclear excited state, the solid need not be crystalline. Mossbauer effects have been observed in amorphous materials and even liquids of high viscosity. If f is the probability of a recoilless event, also known as the Debye-Waller factor, it has been shown that $$f = \exp\left(\frac{-4\pi^2 <r^2>}{\lambda^2}\right) \quad (3)$$

where $<r^2>$ is the square of the displacement of the emitting or absorbing atom from its equilibrium position along the direction of the gamma ray momentum, averaged over the lifetime of the nuclear excited state; $\lambda$ is the wavelength of the radiation. It can be seen from Equation 3 that f is large when the scattering center is confined to a region small with respect to the wavelength of the radiation involved. $<r^2<$ decreases with increasing lattice binding energy; it also decreases as the temperature is lowered.

The Debye-Waller factor has been calculated for a crystal in which the forces are harmonic, using the Debye model of a solid:

$$f = \exp\left\{-3/2\, Eo^2/2Mc^2 \cdot \left[1/K\sigma\, 1 + 2/3\left(\frac{\pi T}{\sigma}\right)^2\right]\right\} \quad (4)$$

in which T is the Debye temperature, M is the atomic mass, K is the Boltzmann constant, and Eo is the gamma ray energy. The recoil energy in the case of Fe-57 used as an absorber pharmaceutical is $2 \times 10^{-6}$ eV; this is well below the average vibrational energy at room temperature ($\sim 10^{-2}$ eV). The low recoil energy coupled with relatively high Debye temperatures for iron complexes (e.g., $\sigma = 355°$ C. for Fe metal) makes Fe-57 particularly suitable for Mossbauer absorption. The Debye-Waller factor for Fe-57 in metallic iron is 0.7 at room temperaure.

In the low temperature limit $$f = \exp\left[-3/2\, \frac{Eo/2Mc^2}{K\sigma}\right] \quad (5)$$

It can be seen from Equation 5 that when the free atom recoil energy is less than $K\sigma$, which is the average energy of a lattice vibrational mode, a recoil-free event has a high probability of occurring. At 5° K.$\sigma$ the value of f in oxyhemoglobin has been found experimentally to be 0.83. The recoil energy due to absorption of a 14.4 KeV photon by hemoglobin is $2 \times 10^{-6}$ eV; the recoil energy of Cytochrome c embedded in a protein matrix would be expected to be less; as would that of nuclear DNA to which a Mossbauer pharmaceutical is bound. Thus, it would more closely approach the line width.

The absorption cross section for gamma to produce a transition between nuclear ground and excited states at resonances followed by fluorescent emission is given by $$\sigma = \frac{1}{2\pi} \frac{h^2 c^2}{E_o^2} \frac{2I_e + 1}{2I_g + 1} \frac{1}{1 + \alpha} \quad (6)$$

where h is Planck's constant, c is the velocity of light, $E_o$ is the transition energy, $I_e$ and $I_g$ are the excited and ground state spins, respectively, and $\alpha$ is the internal conversion coefficient ($\alpha$ describes the relative strength of radiative (gamma ray) and nonradiative (electron conversion) processes connecting the ground and excited states; $\alpha = 0$ if all the decays from the excited state involve the emission of a gamma ray). Thus the cross-section for the electron conversion process is $\alpha$ times the radiative cross-section. The fact that this cross-section is dependent entirely on nuclear parameters is an important and useful feature of the Mossbauer effect. For a single $Fe^{57}$ nucleus, $\sigma_o$ has the value $2.5 \times 10^{-18}$ $cm^2$ for the 14.4 KeV transition. This cross section is about $10^6$ times larger than the actual geometrical cross-section of the nucleus and is also very large compared to the photoelectric (electronic) absorption cross-section for iron, which is $5.5 \times 10^{-21}$ $cm^2$ per atom at this energy. The absorption is an exponential function of the cross-section; thus, the nuclear resonance absorption process is a strong effect.

THE APPARATUS

The overall operation of the system may be exemplified by the $Co^{57}/Fe^{57}$ pair as follows: the radioactive source in the form of a thin film of material such as stainless steel, copper, or palladium into which radioactive Co-57 has been allowed to diffuse produces a beam of light homogeneous photons having an average energy of 14.4 KeV. The homogeneity, or line width $\Delta E$ is $4.5 \times 10^{-9}$ eV so that $\Delta E/E$ is less than $10^{-12}$. A filter selects the 14.4 KeV photon from the other two photons of different energy.

By mounting the sources on an accurately controlled mass drive, the energy of the photon is shifted by means of the Doppler effect. A velocity of 1 mm/sec corresponds to an energy change of $4.8 \times 10^{-8}$ eV or more than ten line widths. A wide variety of velocity drives exist. The arrangement 100 shown in FIG. 1 is one in which the source 50 is mounted on a cone 62 of a speaker 60 and the speaker is driven so that the velocity increases and decreases linearly with time (symmetric triangular wave form) at approximately 5 Hz. Since the displacement of the speaker coil is quite closely proportional to the input voltage, it is necessary to provide a ramp voltage in order to produce a linear velocity. This is accomplished by a triangular wave. A function generator 54 is employed to produce an accurate, low frequency triangular voltage. This voltage is applied to the speaker 60 through a power amplifier 56. In practice, it is necessary to employ considerable negative feedback to produce an accurately linear velocity. This is accomplished by coupling a second (or using a double voice coil 64) speaker 66 to the drive speaker 60 with a rigid rod 52, and providing the error signal from the second speaker (monitored by oscilloscope 58) to the amplifier 56 through the integrator 68 as shown schematically in FIG. 1. The source 50 is mounted on the rod connecting the two speakers.

Since the source executes two velocity extrusions, one at positive and one at negative accelerations, a synchronized shutter 70 can be used to block radiation during the nonresonant excursion.

The source, or emitter of radiation, can also include the techniques known to Mossbauer spectrometry, with the addition of a single frequency filter 80. The filter 80, receives source 70 radiation through an input collimator 82 and enters a diffraction crystal 84. Since the diffraction angle can be calculated (Bragg equation $n\lambda = 2d \sin \theta$), the desired frequency is selected by placement of a second output collimator 86 and the selection of a crystal having an appropriate intranuclear layer distance (d).

In addition to the above-mentioned photon sources, the photon emitters of Table 1 listed further below are useful in conjunction with the correspondingly listed absorbers.

Fluorescence, or nuclear emissions of the tissue components excited at the Mossbauer frequency can also be observed from the target area. The dynamic range (signal-to-noise) can be enhanced by viewing the subject 90 off-axis from the incident radiation from the source, thereby eliminating the background level (from the source). Off-axis viewing is possible due to the nondirectional characteristic of the fluorescence of the target tissue component at the Mossbauer frequency. Moreover, the frequency of the fluorescence will coincide with the frequency of the source due to the narrow spectrum of the Mossbauer resonance. Also due to the finite half life of the excited state, fluorescence can be discriminated from exciting radiation by timing the arrival of the signals.

Furthermore, the fluorescence can be continuously monitored by sensor 92 to give a characteristic plot of the treatment effectiveness. A control signal can be derived from such fluorescence, and combined or processed by processor 94 according to the characteristic plot to continuously control the source to optimize the therapy treatment.

IMAGE SCANNING

All Mossbauer isotopes are gamma emitters following absorption of the same energy gamma photon, and most are stable isotopes; therefore, they can be used in scintiscans. As in the case of radionuclides, information can be gained based on differential uptake, excretion, or concentration as a consequence of the physiology of the pathological process. But Mossbauer scintiscans also provide the ability to diagnose disease processes and to selectively image different tissues based on the phenomenon of the differential resonance frequency of the absorber istope in different tissue environments. Exciting the absorber isotope or isotopes by causing a selected Doppler shifted emission from the emitter or emitters along one axis and simultaneously scanning with conventional sciniscan instrumentation along an axis different from the former axis produces a Mossbauer Isotopic Resonance Absorption of Gamma Emission ((MIRAGE) scintisan. Due to attenuation of the exciting beam as a function of distance along the emitting axis, a correction algorithm has to be used to process the data to produce an image of the actual distribution of the Mossbauer istope or isotopes in the tissue.

Radionucleotides, which have short half lives, on the order of hours, and which are gamma-emitting isotopes, are used in scintiscans to gain diagnostic information based on the physiological properties of the pathological process. These properties include differential uptake, concentrations, or excretion of the radionucleotide by normal versus diseased tissue. For example, hepatic scintiscans are performed with gamma-emitting isotopes that are extracted selectively by the liver, followed by external radiation scanning of the upper abdomen. There are basically three types of liver scans: the colloidal scan, which depends on uptake of labelled colloid by Kupper cells, where $^{198}$Au colloidal gold or $^{99m}$Tc sulfur colloid is most commonly used; the HIDA or PIPIDA scans ($^{99m}$Tc-labelled N-substituted iminoacetitic acids) in which the dye is taken up and excreted by hepatocytes, and the gallium scan, in which the radionuclide $^{67}$Ga is concentrated in neoplastic or inflammatory cells to a greater degree than in hepatocytes. Hence, a hepatoma or liver abscess will produce an area of reduced uptake or "hole" using colloid or HIDA or PIPIDA scans, but there will be an area of increased uptake or "hot spot" with a gallium scan. The gallium scan is also helpful in diagnosing neoplastic infiltration in the patient with cirrhosis, since the tumor will show increased uptake, while fibrous bands will show decreased uptake. Another major application of HIDA or PIPIDA liver scans is in the diagnosis of acute cholecystitis, where failure of the nuclide to enter the gall bladder is considered evidence of cystic duct or common bile duct obstruction. The normal physiology involved is the uptake of these compounds by the hepatocytes followed by excretion into the biliary canaliculi and concentration in the gall bladder.

PHARMACEUTICALS

A number of pharmaceutical isotopes show the Mossbauer effect and a change of absorption frequency in tissue. The stable isotope Fe-57 demonstrates this effect, thus cytochrome c which contains Fe can be selected as a target for Mossbauer absorption. Cytochrome c is a heme protein found in the mitochrondria of mammalian cells. It constitutes about 1 wt% of mitochrondrial protein (*Journal of Bioenergetics and Biomem.*), and is involved in the respiration of aerobic organisms and tissues. It has a molecular weight between 12,000 and 13,000 and one heme group per molecule. At least three bonds link the heme to the protein in Cytochrome c; one is thought to be an iron protein bond and two are covalent bonds to the prophyrin ring.

To obtain Fe-57 in the proper excited state, it is necessary to use the radioactive isotope Co-57 which decays with a half life of 270 days, to the 136 KeV excited state of Fe-57; the latter nucleus in decaying to its own ground state emits three gamma rays, one of which has an energy of 14.4 KeV which has the characteristics suitable for Mossbauer absorption.

In Fe-57, the 14.4 KeV level has a mean life of $1.0 \times 10^{-7}$ sec of a level width of $4.5 \times 10^{-9}$ eV, so that when $Co^{57}$ is embedded in a nonmagnetic solid, the 14.4 KeV photons have a special homogeneity of three parts in $10^{-13}$. As a consequence, hyperfine interactions as a small as $10^{-8}$ eV become accessible to selective absorption by Mossbauer effects. Furthermore, Cytochrome c is strongly bound to a heavy molecule which is embedded in a protein matrix and thus is accessible as a target by this effect.

Furthermore, iron occurs in a distinct environment (or prosthetic group) in several molecules, e.g., the heme group occurs in hemoglobin, myoglobin, peroxidases, and catalasas as well as in cytochromes. In addition, many biological molecules contain Fe at their active centers. Thus, the potential of using this isoptope as a target of therapy is not limited to cytochromes. For example, spectra of red blood cells demonstrate that the absorption spectrum of deoxyhemoglobin is significantly different from that of oxyhemoglobin. This property may be used to treat large tumors which have outgrown their blood supply and are therefore ischemic. By irradiating at the deox Hb Doppler frequency, the gamma rays would be selectively absorbed by red blood cells present in vessels supplying the tumor. Coagulation secondary to damage to those cells would result in thrombosis of the blood supply to the tumor and concomitant tumor death.

Fe-57 occurs with a natural abundance of 2.2%. Furthermore, the total body iron stores are about 4 g and the turnover rate is about 1 mg/day. Patients who consume Fe-57 would incorporte this isotope in cells which have a rapid turnover rate. Cancer cells would be enriched relative to normal cells.

Many other stable isotopes demonstrate recoilless absorption of gamma ray photons following recoilles emission from the corresponding decaying isotope. The stable isotopes appear in Table 1. As exemplified by iron, these isotopes may be substitutetd into natural biological molecules or may be incorporated into a target tissue as non-naturally occurring pharmaceutical molecules.

TABLE 1

| Absorber | Source(s) | | |
|---|---|---|---|
| $^{176}$Yb | $^{176}$Tm | | |
| $^{159}$Tb | $^{159}$Gd | $^{159}$Dy | |
| $^{165}$Ho | $^{165}$Dy | $^{165}$Yb | |
| $^{231}$Pa | $^{231}$Th | $^{231}$U | |
| $^{157}$Gd | $^{157}$Eu | $^{157}$Tb | |
| $^{164}$Er | $^{164}$Ho | $^{164}$Tm | |
| $^{168}$Er | $^{168}$Ho | $^{168}$Tm | |
| Tc$^{99}$ | Mo$^{99}$ | | |
| Gd$^{156}$ | Eu$^{156}$ | Tb$^{156}$ | |
| Gd$^{154}$ | Eu$^{154}$ | Tb$^{154}$ | |
| Er$^{167}$ | Ho$^{167}$ | Tm$^{167}$ | |
| $_{68}$Er$^{170}$ | Ho$^{170}$ | Tm$^{170}$ | |
| Sm$^{152}$ | Pm$^{152}$ | Eu$^{152m}$ | Eu$^{152}$ |
| Hf$^{176}$ | Lu$^{176m}$ | Ta$^{176}$ | Lu$^{176}$ |
| Tm$^{169}$ | Er$^{169}$ | Yb$^{169}$ | |
| U$^{238}$ | Pu$^{242}$ | | |
| Sm$^{151}$ | Pm$^{151}$ | | |
| Sm$^{153}$ | Pm$^{153}$ | | |
| $_{62}$Sm$^{154}$ | Pm$^{154}$ | Eu$^{154}$ | |
| Pr$^{141}$ | Ce$^{141}$ | Nd$^{141}$ | |
| Os$^{186}$ | Re$^{186}$ | Ir$^{186}$ | |
| Os$^{188}$ | Re$^{188}$ | Ir$^{188}$ | |
| Hf$^{177}$ | Lu$^{177m}$ | Ta$^{177}$ | Lu$^{177}$ |
| Lu$^{175}$ | Yb$^{175}$ | Hf$^{175}$ | |
| Gd$^{160}$ | Eu$^{160}$ | | |
| Hf$^{178}$ | Lu$^{178}$ | Ta$^{178}$ | |
| Gd$^{158}$ | Eu$^{158}$ | Tb$^{158}$ | |
| Er$^{166}$ | Ho$^{166m}$ | Tm$^{166}$ | Ho$^{166}$ |
| Cs$^{133}$ | La$^{133}$ | Ba$^{133}$ | Xe$^{133}$ |
| $^{174}$Yb | $^{174m}$Tm | $^{174}$Lu | $^{174}$Tm |
| $^{67}$Zn | $^{67}$Cu | $^{67}$Ga | |
| $^{172}$Yb | $^{172}$Tm | $^{172}$Lu | |
| $^{171}$Yb | $^{171}$Tm | $^{171}$Lu | |

TABLE 1-continued

| Absorber | Source(s) | | | |
|---|---|---|---|---|
| $^{170}$Yb | $^{170}$Tm | $^{170}$Lu | | |
| $^{131}$Xe | $^{131}$I | $^{131}$Cs | | |
| $^{186}$W | $^{186}$Ta | $^{186}$Re | | |
| $^{184}$W | $^{184}$Ta | $^{184m}$Re | $^{184}$Re | |
| $^{183}$W | $^{183}$Ta | $^{183}$Re | | |
| $^{182}$W | $^{182}$Ta | $^{182}$Re | | |
| $^{180}$W | $^{180m}$Ta | $^{180}$Re | $^{180}$Ta | |
| $^{232}$Th($^{228}$Ra) | $^{236}$U | | | |
| $^{236}$U | $^{236}$Pa | $^{240}$Pu | $^{236}$Np | |
| $^{181}$Ta | $^{181}$Hf | $^{181}$W | | |
| $^{125}$Te | $^{125}$Sb | $^{125}$I | | |
| $^{147}$Pm | $^{147}$Pm | $^{147}$Eu | | |
| $^{149}$Sm($^{145}$Nd) | $^{149}$Pm | $^{149}$Eo | | |
| $^{101}$Ru | $^{101}$Tc | $^{101m}$Rh | $^{101}$Rh | |
| $^{99}$Ru | $^{99}$Tc | $^{99m}$Rh | $^{99}$Rh | |
| $^{195}$Pt | $^{195m}$Ir | $^{195}$Au | $^{195}$IR | $^{195m}$Pt |
| $^{147}$Pm($^{147}$Sm) | $^{147}$Nd | | | |
| $^{189}$Os | $^{189}$Re | $^{189}$Ir | | |
| $^{237}$Np($^{233}$Pa) | $^{237}$U | $^{241}$Am | $^{237}$Pu | |
| $^{61}$Ni | $^{61}$Co | $^{61}$Cu | | |
| $^{83}$Kr | $^{83}$Br | $^{83}$Rb | $^{83m}$Kr | |
| $^{193}$Ir | $^{193}$Os | $^{193}$Pt | | |
| $^{191}$Ir | $^{191}$Os | $^{191}$Pt | | |
| $^{201}$Hg | $^{201}$Au | $^{201}$Ti | | |
| $^{180}$Hf | $^{180}$Lu | $^{180m}$Ta | $^{180}$Ta | |
| $^{139}$La | $^{139}$Ba | $^{139}$Ce | | |
| $^{187}$Re | $^{187}$W | | | |
| $^{234}$U | $^{234m}$Pa | $^{238}$Pu | $^{234}$Np | $^{234}$Pa |
| $^{236}$U | $^{236}$Pa | $^{240}$Pu | $^{236}$Np | |
| $^{239}$Pu | $^{239}$Np | $^{234}$Cm | $^{239}$Am | |
| $^{190}$Os | $^{190}$Re | $^{190}$Ir | | |
| $^{197}$Au | $^{197}$Pt | $^{197}$Hg | | |
| $^{133}$Cs | $^{133}$Xe | $^{133}$Ba | | |
| $^{160}$Dy | $^{160}$Tb | $^{160}$Ho | | |
| $^{166}$Er | $^{166m}$Ho | $^{166}$Tm | $^{166}$Ho | |
| $^{155}$Gd | $^{155}$Eu | $^{155}$Tb | | |
| $^{73}$Ge | $^{73}$Ga | $^{73}$As | | |
| $^{178}$Hf | $^{178}$Lu | $^{178}$Ta | | |
| K$^{40}$ | | | | |
| Am$^{243}$ | Pu$^{243}$ | Bk$^{247}$ | | |
| $^{145}$Nd | $^{145}$Pr | $^{145}$Pm | | |
| $^{153}$Eu | $^{153}$Sm | $^{153}$Gd | | |
| $^{129}$I($^{129}$Xe) | $^{129m}$Te | | | |
| $^{127}$I | $^{127}$Te | $^{127}$Xe | | |
| $^{119}$Sn | $^{119m}$In | $^{119}$Sb | $^{119}$Tn | |
| $^{57}$Fe | $^{57}$Mn | $^{57}$Co | | |
| $^{151}$Eu | $^{151}$Sm | $^{151}$Gd | | |
| $^{129}$Xe | $^{129}$I | $^{129}$Cs | | |
| $^{164}$Dy | $^{164}$Tb | $^{164}$Ho | | |
| $^{57}$Fe | $^{57}$Mn | $^{57}$Co | | |
| $^{161}$Dy | $^{161}$Tb | $^{161}$Ho | | |
| $^{162}$Dy | $^{162}$Tb | $^{162}$Ho | | |
| $^{117}$Sn | | | | |
| $^{121}$Sb | $^{121m}$Sn | $^{121}$Sn | $^{121m}$Te | $^{121}$Te |
| $^{127}$I | $^{127}$Te | $^{127}$Xe | | |
| $^{129}$I | $^{129}$Te | $^{129m}$Te | | |
| $^{133}$Ba | $^{133}$La | | | |
| $^{145}$Nd | $^{145}$Pr | $^{145}$Pm | | |
| $^{145}$Pm | | | | |
| $^{147}$Sm | $^{147}$Pm | $^{147}$Eu | | |
| $^{153}$Eu | $^{153}$Sm | $^{153}$Gd | | |

These Mossbauer isotopes could be used to replace the same element, e.g., $^{127}$I and $^{129}$I could be used in hormones or $^{67}$Zn in enzymes. Also, Mossbauer isotopes could be used to substitute for a different element, e.g., $^{133}$Cs could be substituted for Na$^+$ and K$^+$ or $^{151}$Eu and $^{151}$Eu$^{2+}$ could be used as a substitute for Ca$^{2+}$ in bone. Furthermore, many possibilities exist for developing pharmaceuticals which behave differently in different cell types to cause differential uptake and binding of a Mossbauer atom or molecule incorporating one or more Mossbauer atoms to selected sites in the tumor cells, for example. Large local concentrations could be achieved through this process. $^{57}$Fe bleomycin, for example, has an association constant for DNA of $10^6$, and a molucule of this drug is bound for every eight nucleotides. $^{119}$Sn $^{2+}$ is a candidate for binding to DNA, which is negatively charged. For $^{119}$Sn, $^{119m}$Sn could be incorporated into a BaSnO$_3$ matrix to constitute the emitter. A Pd filter would remove particles, and the pharmaceutical could be a salt of $^{119}$Sn$^{2+}$. $^{131}$Xe or $^{129}$Xe which are membrane-soluble could be used to localize into the nuclear, mitochondrial or cellular membrane. Furthermore, experiments have shown that molecules or atoms which are dissolved into membranes or bound or absorbed to cellular structures undergo recoilless absorption. (Evan et al. 1977 and Giberman et al. 1974).

TISSUE SELECTIVE THERAPY

Bone tumors and bone metastases cna be treated by the incorporation of a Mossbauer absorber into bone. Recoilless absorption will occur when the isotope becomes part of the bone matrix. Emission Mossbauer nuclide for $^{133}$Cs is $^{133}$Ba. Mashall (1968) has obtained a Mossbauer spectrum with a $^{133}$CsF absorber and a source provided by $^{133}$Ba fixed onto bone powder by incubation of the latter in a solution of radioactive $^{133}$BaCl$_2$.

In addition to the alkaline earths, the rare earths are also "bone seekers." Kellershohn et al. (1974, 1979) have investigated both in vivo and in vitro fixation of rear earths onto bone material using $^{161}$Dy Mossbauer spectroscopy. Excellent spectra are obtained at room temperature indicating that the rare earth element is metabolically fixed onto the bone and is actually incorporated into a solid structure. Another pharmaceutical is $^{151}$Eu or $^{153}$Eu since both atoms can be isoelectronic with Ca$^{2+}$. $^{149}$Sm has a very significant Mossbauer cross-section of $3.7 \times 10^{-18}$ and $^{149}$Sm is also a rare earth "bone seeking" candidate for the metabolic incorporation at sites of new bone formation secondary to metastatic or primary bone cancer.

Also, pharmaceuticals could be snythesized using these isotopes such that the Mossbauer absorption occurs at a Doppler frequency in the cancer cells which is different from that of normal cells. The difference in chemical environments between normal and cancer cells results in alternate conformation, protonation, charge, etc. of the properly constructed therapeutic molecule so that the s electron density at the Mossbauer nucleus is altered. The difference is s electron density results in a difference in the nuclear transition energy with a concomitant frequency difference of absorbed photons.

ENERGY/FREQUENCY SELECTIVE THERAPY

The Mossbauer absorption spectrum of a biopsy of normal and malignant tissue would yield the Doppler shifted frequencies that would result in selective gamma ray absorption in the malignant tissue. The apparatus and methods according to the present invention also select the source frequency to optimize the cell damage or kill when different from the actual Mossbauer absorption of the target tissue.

The photoelectric and Compton cross-sections are summarized in Table 2 which contains the mass energy absorption coefficients in the absence of the Mossbauer effects. The equation for determining the total dose from gamma ray treatment and the depth of penetration of the photons appears in Equation (11). Equation (11) and Table 2 demonstrate the relationship that photons of higher energy penetrate deeper into tissue. Since the different Mossbauer isotopes demonstrate a wide range of photon energies, therapies can be designed to exploit this phenomenon to deliver the energy of the radiation to a selected depth. For example, the 14.4 KeV gamma ray of $^{57}$Fe with a mass energy tissue absorption coefficient of 1.32 cm$^2$/gm would be suitable for intraoperative radiation of breast, bowel, and pancreatic cancer, whereas the 60 KeV gamma ray of $^{155}$Gd with a mass energy bone absorption coefficient of 0.03 cm$^2$/gm represents a suitable isotope for the treatment of primary and metastatic bone cancer.

$$\theta_o = \frac{1}{2\pi} \frac{h^2C^2}{Eo^2} \frac{2Ie + 1}{2Ig - 1} \frac{1}{1 + \alpha} \quad (7)$$

where h is Planck's constant, C is the velocity of light, Eo is the transition energy, Ie and Ig are the excited and ground spins, respectively, and $\alpha$ is the internal conversion coefficient. $\alpha$ is the ratio of the intensity of the fluoroscent processes connecting the ground and excited states. This cross section is dependent entirely on nuclear parameters. The Auger process is the phenomenon useful in cancer therapy and the Mossbauer nuclear cross sections of absorption followed by internal conversion of some representative isotopes given by $\alpha\theta$ appears in Table 3.

The fluorescent absorption cross section for $\gamma$-rays to produce a transition between nuclear ground and excited states at resonance is given by:

TABLE 2

MASS ENERGY ABSORPTION COEFFICIENTS

| Photon Energy Mev | H | C | N | O | Na | Mg | P | S |
|---|---|---|---|---|---|---|---|---|
| 0.010 | 0.0092 | 1.91 | 3.42 | 5.50 | 15.4 | 20.9 | 40.1 | 49.7 |
| 0.15 | 0.0110 | 0.517 | 0.916 | 1.49 | 4.43 | 6.09 | 11.9 | 15.2 |
| 0.020 | 0.0133 | 0.203 | 0.360 | 0.587 | 1.77 | 2.47 | 5.00 | 6.11 |
| 0.030 | 0.0186 | 0.0592 | 0.102 | 0.163 | 0.182 | 0.684 | 1.45 | 1.85 |
| 0.040 | 0.0230 | 0.0360 | 0.0165 | 0.0700 | 0.191 | 0.274 | 0.570 | 0.731 |
| 0.050 | 0.0270 | 0.0226 | 0.0299 | 0.0410 | 0.0996 | 0.140 | 0.282 | 0.361 |
| 0.060 | 0.0305 | 0.0203 | 0.0244 | 0.0301 | 0.0637 | 0.0845 | 0.166 | 0.214 |
| 0.080 | 0.0362 | 0.0201 | 0.0218 | 0.0239 | 0.0369 | 0.0156 | 0.0780 | 0.0971 |
| 0.10 | 0.0106 | 0.0213 | 0.0222 | 0.0232 | 0.0288 | 0.0331 | 0.0500 | 0.0599 |
| 0.15 | 0.0185 | 0.0246 | 0.0219 | 0.0252 | 0.0258 | 0.0275 | 0.0315 | 0.0351 |
| 0.20 | 0.0530 | 0.0267 | 0.0267 | 0.0271 | 0.0265 | 0.0277 | 0.0292 | 0.0310 |
| 0.30 | 0.0573 | 0.0288 | 0.0289 | 0.0289 | 0.0278 | 0.0290 | 0.0290 | 0.0301 |
| 0.40 | 0.0587 | 0.0295 | 0.0296 | 0.0296 | 0.0283 | 0.0295 | 0.0290 | 0.0301 |
| 0.50 | 0.0589 | 0.0297 | 0.0297 | 0.0297 | 0.0284 | 0.0293 | 0.0288 | 0.0300 |
| 0.60 | 0.0588 | 0.0296 | 0.0296 | 0.0296 | 0.0283 | 0.0292 | 0.0287 | 0.0297 |
| 0.80 | 0.0573 | 0.0288 | 0.0289 | 0.0289 | 0.0276 | 0.0285 | 0.0280 | 0.0287 |
| 1.0 | 0.0555 | 0.0279 | 0.0280 | 0.0280 | 0.0267 | 0.0275 | 0.0270 | 0.0280 |
| 1.5 | 0.0507 | 0.0255 | 0.0255 | 0.0255 | 0.0243 | 0.0250 | 0.0245 | 0.0251 |
| 2.0 | 0.0161 | 0.0234 | 0.0234 | 0.0234 | 0.0225 | 0.0232 | 0.0228 | 0.0235 |
| 3.0 | 0.0398 | 0.0204 | 0.0205 | 0.0206 | 0.0199 | 0.0206 | 0.0201 | 0.0210 |
| 4.0 | 0.0351 | 0.0184 | 0.0186 | 0.0187 | 0.0181 | 0.0191 | 0.0192 | 0.0199 |
| 5.0 | 0.0316 | 0.0170 | 0.0172 | 0.0174 | 0.0173 | 0.0181 | 0.0184 | 0.0192 |
| 6.0 | 0.0288 | 0.0160 | 0.0162 | 0.0166 | 0.0166 | 0.0175 | 0.0179 | 0.0187 |
| 8.0 | 0.0249 | 0.0145 | 0.0148 | 0.0154 | 0.0158 | 0.0167 | 0.0175 | 0.0181 |
| 10.0 | 0.0222 | 0.0137 | 0.0142 | 0.0147 | 0.0154 | 0.0163 | 0.0174 | 0.0183 |

| Mev | A | K | C.. | Water | Air | Bone | Muscle | MASS ENERGY ABSORPTION COEFFICIENTS ($\mu_{en}$) [cm$^2$/gm] |
|---|---|---|---|---|---|---|---|---|
| 0.010 | 62.0 | 77.0 | 89.8 | 4.89 | 4.66 | 19.0 | 4.96 | |
| 0.015 | 19.4 | 24.6 | 28.9 | 1.32 | 1.29 | 5.89 | 1.36 | |
| 0.020 | 8.31 | 10.5 | 12.5 | 0.523 | 0.516 | 2.51 | 0.544 | |
| 0.030 | 2.46 | 3.12 | 3.75 | 0.147 | 0.147 | 0.743 | 0.151 | |
| 0.040 | 0.974 | 1.25 | 1.52 | 0.0617 | 0.0610 | 0.305 | 0.0677 | |
| 0.050 | 0.484 | 0.626 | 0.761 | 0.0394 | 0.0381 | 0.158 | 0.0409 | |
| 0.060 | 0.281 | 0.367 | 0.443 | 0.0304 | 0.292 | 0.0979 | 0.0312 | |
| 0.080 | 0.124 | 0.158 | 0.191 | 0.0253 | 0.0230 | 0.0520 | 0.0255 | |
| 0.10 | 0.0725 | 0.0909 | 0.111 | 0.0252 | 0.0231 | 0.0386 | 0.0252 | |
| 0.15 | 0.0368 | 0.0133 | 0.0188 | 0.0278 | 0.0251 | 0.0301 | 0.0276 | |
| 0.20 | 0.0302 | 0.0339 | 0.0367 | 0.0300 | 0.0268 | 0.0302 | 0.0297 | |
| 0.30 | 0.0278 | 0.0304 | 0.0319 | 0.0320 | 0.0288 | 0.0311 | 0.0317 | |
| 0.40 | 0.0271 | 0.0299 | 0.0308 | 0.0329 | 0.0296 | 0.0316 | 0.0325 | |
| 0.50 | 0.0271 | 0.0291 | 0.0301 | 0.0330 | 0.0297 | 0.0316 | 0.0327 | |
| 0.60 | 0.270 | 0.0291 | 0.0301 | 0.0329 | 0.0296 | 0.0315 | 0.0326 | |
| 0.80 | 0.0261 | 0.0282 | 0.0290 | 0.0321 | 0.0289 | 0.0306 | 0.0318 | |
| 1.0 | 0.0252 | 0.0272 | 0.0279 | 0.0311 | 0.2380 | 0.0297 | 0.0308 | |
| 1.5 | 0.0228 | 0.0247 | 0.0253 | 0.0283 | 0.0255 | 0.0270 | 0.0281 | |
| 2.0 | 0.0212 | 0.0228 | 0.0234 | 0.0260 | 0.0234 | 0.0218 | 0.0257 | |
| 3.0 | 0.0193 | 0.0208 | 0.0213 | 0.0227 | 0.0205 | 0.0219 | 0.0225 | |
| 4.0 | 0.0182 | 0.0199 | 0.0204 | 0.0205 | 0.0186 | 0.0199 | 0.0203 | |
| 5.0 | 0.0176 | 0.0193 | 0.0200 | 0.0190 | 0.0173 | 0.0186 | 0.0188 | |
| 6.0 | 0.0175 | 0.0190 | 0.0198 | 0.0180 | 0.0163 | 0.0178 | 0.0178 | |
| 8.0 | 0.0172 | 0.0190 | 0.0197 | 0.0165 | 0.0150 | 0.0165 | 0.0163 | |
| 10.0 | 0.0173 | 0.0191 | 0.0201 | 0.0155 | 0.0141 | 0.0159 | 0.0154 | |

$\theta$ is the maximum value of the resonance absorption cross section. The energy dependent cross section is given by:

$$\theta = \theta_o [1 + 4(E - Er)^2/\Gamma^2]^{-1} \quad (8)$$

where E is the incident $\gamma$-ray energy and $\Gamma$ is the uncertainty-principle energy width of the excited state. This width is defined by $\Gamma = h/2\pi T$, where T is the meanlife (=1.44×the half life) of the excited state. The values of the minimum Mossbauer line width of some representative isotopes appears in Table 3.

The Mossbauer phenomenon has an extremely narrow line width to energy ratio that can distinguish between sets of absorbers, but the line is not too narrow to preclude resonance within a set where some atom to atom variability of resonance energy occurs.

For a gamma ray to be resonantly absorbed, the event must occur without recoil energy loss. The fraction of atoms which undergoes recoilless absorption is called the recoil free fraction which can be approximated by the following equation $$f \approx \exp\left(-\frac{CErT}{K\theta_o^2}\right) \quad (9)$$

flux, $\phi$. The number of Auger events, $\alpha$, for the absorber is given by $$\alpha = \phi n f \theta \quad (10)$$

Since Mossbauer absorbers are radioactive, atoms following the absorption event, experiments involving radioactive atoms should predict the outcome of the same experiment where Mossbauer atoms are substituted. As specified by Linz and Stoecklin, "Seventh International Congress of Radiation Research, " U. Linz and G. Stoecklin, Amsterdam, 1983, with $I^{125}$ labeled iododeoxycytidine it was found that always greater than two and as many as twelve double strand breaks occurred in a DNA fragment per decay event. Cells are very susceptible to double strand breaks and one event which produces a double strand break could kill a cell. Conventional radiation therapy relies on nonspecific ionization and free radical production where $H_2O$ is the primary target. If the total dose is 6,000 rads, then the number of absorption/ionization events is approximately $2 \times 10^5$/cell for treatment with a 25 keV photon which has a mass energy absorption coefficient of approximately 0.3. In this determination, the volume of a cell was taken as $4 \times 10^{-9}$ cm$^3$ and the following equation was used:

| TOTAL ABSORBED DOSAGE: | From a source of A Ci, at a constant distance of r cm., of an isotope with mean life T, where exposure occurs for durations u, starting at intervals of v and occurring n separate times on an organ of surface area S, density $\rho$ due to gamma rays emitted by the decays which have individual energies of E MeV and for which the organ's tissue have an energy absorption coefficient of $\mu_{en}$ cm/gram. |
|---|---|

$$= A\ Ci \times 3.7 \times 10^{10} \frac{counts}{sec\text{-}Ci} \times T\ sec \quad \times (1 - e^{-u/T}) \frac{(1 - e^{-nv/T})}{(1 - e^{-v/T})}$$

| original count rate at t = 0 |
| number of nuclei present at t = 0 | × | fraction of original nuclei that will decay during the n intervals of duration u, separation v.
| total number of decays that occur during periods of exposure |

$$\times \frac{S}{4\pi r^2} \quad \times (1 - e^{-\mu_{en}\rho dr}) \quad \times E\ MeV \times 1.6 \times 10^{-6} \frac{erg}{MeV} \times \frac{1}{\rho Sdr} \times \frac{1}{100} \quad (5)\ (11)$$

| fraction of rays emitted from source that will pass through surface area, S, of organ at distance r. | fraction of ray's energy absorbed in passing through a thickness, dr, of tissue | total energy of each ray [ergs] | |
| ... total number of rays that pass through the surface, S. | energy [erg] absorbed in thickness dr of tissue per photon | | ... grams of tissue in thickness dr behind surface, S. |
| | ... total energy absorbed in thickness dr from all photons | | ... total ergs absorbed per gram |
| | | | ... total rads | where Er is the recoil energy of the nuclear transition, T is the temperature, K is the Boltzmann constant and $\theta$ is the characteristic Debye temperature. The recoil free fraction of some representative isotopes appears in Table 3.

The number of gamma rays which are absorbed and undergo internal conversion depends not only on the Auger cross section, but also on the number of absorbing atoms, n, the recoil free fraction, f, and the photon To calculate the reverse value, that is the effective radiation dose for Mossbauer Cancer Therapy, the number of events necessary to kill a cell, 1, drug concentration, 10 $\mu$M, the volume of a cell nucleus, $2 \times 10^{12}$ l, the recoil free fraction for $Sn^{119}$, 0.33, and the Auger cross section for $Sn^{119}$, $716 \times 10^{-20}$ cm$^2$, are used.

$$1 = \phi(.33)(1 \times 10^{-5})(2 \times 10^{-12})(6 \times 10^{-23})(716 \times 10^{-20})$$

-continued $$0 = 3.5 \times 10^{10} \text{ photons which is approximately 3.5 rads.}$$

If the depth of penetration desired is 15 cms and the 24 keV ray of $Sn^{119}$ is used which has a mass energy absorption coefficient of 0.3, then at this depth, the flux would be 0.01 of that of the surface itensity as determined by the following equation:

$$I = I_o e^{-\mu_{en} \rho dx} \qquad (12)$$

The surface dose of 350 rads is only 5.8% of the necessary effective dose by conventional methods and increasing the concentration of the pharmaceutical containing a Mossbauer isotope will directly decrease this ratio. As a consequence of the low dosage of radiation required to be tumoricidal the source can be miniaturized and incorporated into instruments such as laparascopes and brochoscopes to treat locally. Thus, irradiation of normal tissue can be avoided.

Nineteen elements appear in Table 3 which have a large Auger cross section and a high recoil free fraction which culd be used for Mossbauer Cancer Therapy. Several of the isotopes are radioactive, but the half lives of these elements is so low that at the low concentration necessary for therapeutic effectiveness, not even the dose of a radioisotope scitiscan which is about 1 mCi. is exceeded.

Example $t_{\frac{1}{2}}$ for $K^{40} = 1.29 \times 10^9$ years $$(1 \times 10^{-5} M)(7L) \frac{6 \times 10^{23} \text{ atoms}}{\text{mole}} \frac{.693}{1.29 \times 10^9 \text{ yr}} \times \qquad (13)$$

$$\frac{1 \text{ yr}}{3.15 \times 10^7 \text{ sec}} \times \frac{1 \text{ Ci.}}{3.7 \times 10^{10}} \frac{\text{counts}}{\text{sec}} =$$

$$1.9 \times 10^{-8} \text{ Ci} = .02 \, \mu\text{Ci}.$$

Furthermore, selective killing of cancer cells with the sparing of normal cells can be achieved by several mechanisms:

1. The use of pharmaceuticals which are selectively taken up by cancer cells.
2. The use of pharmaceuticals which have a differet isomer shift, quadrapole hf splitting or magnetic hyperfine splitting in cancer cells versus normal cells.
3. Applying magnetic or quadrapole field in the space occupied by the cancer tissue so that a hyperfine absorption line is created for the cancer tissue which is absent for the normal tissue.
4. Polarization of the incident gamma rays with resonant polarization of the absorbers in the cancer tissue and not in the normal tissue.

In the latter case, polarized gamma rays can be obtained by three methods, magnetized ferromagnetic sources, quadrapole split sources, filter techniques as shown by U. Gonser and H. Fischer, Current Topics in Physics Mossbauer Spectroscopy, The Exotic Side of the Method: Resonance $\nu$-Ray Polarimetry, 99-135; incorporated by reference.

FOR CASE, 3 AND 4

Figure 2:
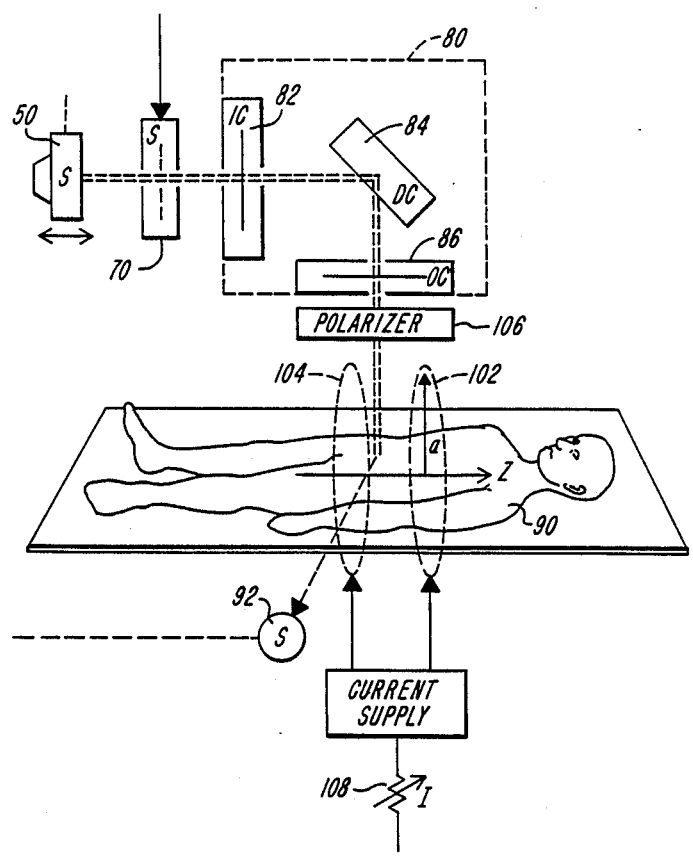
FIG. 2 is an alternate embodiment showing the application of a magnetic field to the subject.

The nuclear spin moment of Mossbauer isotopes become aligned in an imposed magnetic field. Also when a magnetic field exits at the nucleus the nuclear quantum levels are split into sublevels which gives rise to hyperfine interactions and mulitple transition energies between the ground and excited states. The application of a magnetic field in a certain region of space thus creates a new transition for a Mossbauer isotope present in that volume of space. By driving the mass drive 50, FIG. 2, at the proper velocity to produce a gamma ray with the energy of this new transition the atoms in the area where the field was applied selectively absorb the radiation. Also, selective absorption in a predetermined region of space can be accomplished by plane polarizing (106) the source gamma rays and by aligning the absorbing nuclei with an imposed magnetic field in the precise

TABLE 3

| | MOSSBAUER ISOTOPES WITH PARAMETERS FAVORABLE FOR CANCER THERAPY | | | | | | | |
|---|---|---|---|---|---|---|---|---|
| Isotope | Half Life of Ground State (yr)/ Mode of Decay | Isotope Abundance (%) | Gamma Ray Energy (keV) | Half Life of Excited State (NS) | $\alpha$/Auger (Cross-section ($10^{-20}$ cm$^2$) | Mossbauer Line Width (mm/sec) | Recoil Energy ($10^{-3}$ ev) | Recoil Free Fraction $\theta + 300^1$ $\theta_o = 220$ (%) |
| Potassium 40 | $1.28 \times 10^9 \, \beta$ | .012 | 29.5 | 4.25 | 6.6/196 | 2.177 | 11.7 | .6 |
| Iron 57 | | 2.14 | 14.4 | 97.8 | 8.21/2218 | .194 | 1.956 | 44 |
| Tin 119 | | 8.58 | 23.87 | 17.75 | 5.12/716 | .6456 | 2.57 | 33 |
| Antimony 121 | | 57.25 | 37.15 | 3.5 | 11.1/217 | 2.104 | 6.12 | 7 |
| Tellurium 125 | | 6.99 | 35.46 | 1.48 | 13.5/361 | 26.563 | 5.39 | 10 |
| Iodine 127 | | 100 | 57.6 | 1.91 | 3.78/77.5 | 2.486 | 14.0229 | .2 |
| Iodine 129 | $1.7 \times 10^7 \, \beta$ | 0 | 27.77 | 16.80 | 5.1/199 | .586 | 3.2089 | 25 |
| Xenon 129 | | 26.44 | 39.58 | 1.01 | 12.3/288 | 6.84 | 6.5187 | 6 |
| Samarium 149 | $4 \times 10^{14} \, \alpha$ | 13.83 | 22.4940 | 7.12 | 50/372 | 1.708 | 1.8 | 45 |
| Europium 151 | | 47.82 | 21.53 | 9.7 | 30/658 | 1.3 | 1.648 | 46 |
| Gadolinium 155 | | 14.73 | 60.01 | .134 | 8/90.66 | 34.02 | 12.47 | .5 |
| Gadolinium 157 | | 15.68 | 54.54 | .187 | 11.87/114 | 26.82 | 10.17 | 1.2 |
| Gadolinium 157 | | 15.68 | 64.0 | 460 | .7/37 | .009 | 14.004 | .5 |
| Terbium 159 | | 100.0 | 57.955 | .10 | 9.36/98.5 | 44.9 | 11.355 | .8 |
| Dysprosium 161 | | 18.880 | 25.655 | 28.2 | 2.9/275 | .378 | 2.1944 | 38 |
| Dysprosium 161 | | 18.880 | 43.82 | .78 | 4.32/137 | 8.00 | 6.4049 | 5 |
| Dysprosium 163 | | | 26 | | | | | 39 |
| Ytterbium 171 | | 14.31 | 66.72 | .87 | 11.2/100.6 | 4.7127 | 13.97 | .2 |
| Tungsten 183 | | 14.40 | 46.4837 | .184 | 40/220 | 31.98 | 6.3379 | 6.5 |
| Osmium 189 | | 16.1 | 36.22 | .500 | 80/92 | 15.105 | 3.7259 | 20.2 |
| Mercury 201 | | 13.22 | 32.19 | .200 | 60/117 | 42.49 | 2.7672 | 30.4 |
| Thorium 232 | $1.41 \times 10^{10} \, \alpha$ | 0 | 49.369 | .345 | 300/507 | 16.06 | 5.639 | 9 |
| Uranium 238 | $4.5 \times 10^9 \, \alpha$ | 99.27 | 44.915 | .2250 | 660/602 | 27.069 | 4.5499 | 14.3 |
| Neptunium 237 | $2.14 \times 10^8 \, \alpha$ | 0.00 | 59.5370 | 68.3 | 1.12/36 | .0672 | 8.0283 | 3.1 | vector orientation to permit selection of the transition that is of the incident polarization.

Alternatively, the imposed magnetic field may be used to produce an energy transition for absorption of the radiation without the necessity of a doppler shift of the gamma source. The requirement of a magnetic field of predetermined magnitude provided by current adjustment 108 and direction can be accomplished by using Helmholtz coils 102, 104 where the patient 90 is oriented along the z axis of the coils. A uniform field of specific spatial demensions can be created by varying the raduis, a, and the distance, z, between the coils. The individual fields as a function of z are approximately guassian shaped with the addition field being uniform and strongly divergent from uniform immediately adjacent to the uniform region. The equation for the field of the coil is given as follows:

$$H_z = \frac{NI}{2} \frac{a^2}{(a^2 + z^2)^{\frac{3}{2}}} \quad (14)$$

ALTERNATIVE COMBINATIONS OF THERAPEUTIC TREATMENTS

The two major cancer therapies are radiation therapy and chemotherapy. The latter includes agents which can be broken down into six major classes of antitumor agents, alkylating agents, antimetabolites, plant alkaloids, endocrine agents, and immunologic stimulants. Radiation and chemotherapy can be combined synergistically by snythesizing hybrid pharmaceuticals consisting of the active functional groups of chemotherapeutic agents and one or more Mossbauer nuclei per molecule. $^{195}$Pt, cisplatinum, is an example of such a hybrid molecule. Cisplatinum is an alkylating chemotherapeutic agent which becomes covalently bound to DNA. Irradiation at a distinct resonance frequency of Mossbauer nucleus, $^{195}$Pt localized in the tumor cells combines the effects of Mirage therapy with that of chemotherapy to synergistically enhance tumor cell death. Another such example is the hybrid intercalating pharmaceutical, $^{57}$Fe Bleomycin.

As an alternative to selective kill of target cells due to irradiation at a frequency which is resonant only for the isotope localized to the target cell, Mirage therapy could also be made selective by means of developing molecules or ions which are more avidly taken up by the target cells. This constraint is minimized by the relative nontoxicity of any pharmaceutical distributed in nonirradiated areas. Also, the target tissue is irradiated locally; therefore, the enhanced differential uptake would only be relative to other cell populations in the radiation field.

The therapy according to the present invention is useful to treat disease other than cancer. The basis of therapy rests on the selective destruction of one or more cell lines. For example, intra-articular synovectomy using the radionucleotide $^{165}$Dy coupled with a large relatively inert carrier (ferric hydroxide macroaggregate) has been shown by Sledge et al (Sledge, Clement, B., Clinical Orthopedics and Related Research, No. 182, January-February 1984, pp. 37-40) to be an effective means of reducing inflamation, effusion, and pain in patients with rheumatoid arthritis. By using Mossbauer therapy where the stable isotopes $^{161}$Dy or $^{163}$Dy are substituted for $^{165}$Dy and by using local excitation, one side effect of this therapy, systemic irradiation from leakage can be avoided.

Other diseases which can be cured by elimination of specific cell lines include autoimmune diseases and transplant rejection disease, graft versus host, and host versus graft. The cellular mediators for both of these diseases are lymphocytes. The responsible cell lines could be selectively killed by synthesizing hybrid pharmaceuticals consisting of a protein and one or more Mossbauer isotopes. The protein binds to the surface of the target cell in a highly specific manner. A monoclonal antibody to an antigen on the cell surface or a hormone which binds to a receptor on the cell surface could serve as the protein. The tissue is irradiated at the Doppler frequency which is the resonant frequency of the absorber isotopes of the hybrid pharmaceutical molecules bound to the target cells. The subsequently released Auger electrons would destroy the target cells. Thus, the cell line responsible for disease can be eliminated without internalization of the hybrid molecule which is necessary in the case of conventional hybrid pharmaceuticals which consist of a specific binding protein and a toxin.

Modifications and substitutions of system elements by one skilled in the art are considered to be within the scope of the present invention, which is not to be limited except by the claims which follow.

What is claimed is:

1. A method for the treatment of disease by externally and selectively inducing damage or necrosis of target tissue, comprising the steps of:
   determining the Mossbauer absorption frequency of a constituent of said target tissue;
   selecting the Mossbauer absorption frequency of said constituent; and
   exciting said constituent at the selected Mossbauer absorption frequency wherein
   said excited constituent emits radiation causing cell damage of said target tissue.

2. The method of claim 1, wherein the step of exciting said component comprises the step of sufficiently exciting to induce necrosis of said target tissue.

3. The method of claim 2, wherein said step of exciting further comprises
   providing a selective frequency radiation emission from a source; and
   tuning said source to the frequency of the Mossbauer frequency.

4. The method of claim 3, further comprising the step of
   filtering the selective frequency radiation emission from said source to provide a single frequency radiation.

5. The method of claim 3, wherein the step of adjusting the Mossbauer absorption frequency of said excited component includes applying a magnetic field thereon.

6. The method of claim 1, further including the step of
   detecting the radiation emitted by said excited component.

7. The method of claim 6, further including the step of
   adjusting the frequency of said emission according to said detected radiation.

8. The method of claim 7, further including the step of imaging said target tissue according to said detected radiation from said excited component.

9. The method of claim 6, further including the step of
detecting tissue fluoresence along an angle off-axis from the incident radiation.

10. The method of claim 1, further including the step of
administering a pharmaceutical wherein said component selectively absorbs exciting energy at the Mossbauer frequency determined according to at least one of said pharmaceutical and said target tissue.

11. The method of claim 10, wherein
said pharmaceutical comprises an isotope.

12. The method of claim 11, wherein said step of administering further includes
selecting the isotope according to the affinity of said isotope for the target tissue.

13. The method of claim 11, wherein said step of administering further includes
selectively directing the isotope to said target tissue according to the tissue blood flow, wherein a higher concentration of blood provides a greater application of said isotope.

14. The method of claim 11, further comprising the step of
selecting said isotope according to the differential uptake of said target tissue to provide an increased concentration of excited component radiation therein.

15. The method of claim 11, further comprising the step of
selecting said isotope according to the effective penetration depth of the corresponding Mossbauer frequency of said isotope at said target tissue.

16. The method of claim 11, wherein said step of administering includes the step of:
selecting a carrier substance having an affinity for said target tissue; and
bonding said isotope to said carrier substances.

17. The method of claim 16, wherein
said carrier substance comprises one of a monoclonal antibody and a natural hormone.

18. The method of claim 17, further including the step of
combining at least two of said monoclonal antibody, hormone and a toxin.

19. A method for the treatment of disease by externally and selectively inducing damage of target tissue, comprising the steps of:
administering a selected absorber isotope to said target tissue;
emitting a source of radiation at a selected frequency; and
absorbing said radiation at a site of said target tissue causing all damage at said site according to a corresponding Mossbauer frequency and said selected absorber isotope.

20. The method of claim 19, wherein
said absorbers are administered as pharmaceuticals.

21. A method for the treatment of disease by externally and selectively inducing the damage of target tissue, comprising the steps of:
emitting a source of radiation at a selected frequency from a radiation source; and
absorbing said radiation at a site of said target tissue according to the corresponding Mossbauer frequency of a corresponding resonant isotope located at the target tissue causing cell damage at said site.

22. A system for therapeutic radiation of target tissue comprising:
a tunable source providing a selected frequency radiation in response to a magnetic field;
means for applying a magnetic field on said target tissue and said tunable source; and
a Mossbauer absorber located at a site of said target tissue receiving said selected frequency radiate causing cell damage at said site, wherein said Mossbauer absorber includes at least one pharmaceutical of the following list:

$^{176}Yb$
$^{159}Tb$
$^{165}Ho$
$^{231}Pa$
$^{157}Gd$
$^{164}Er$
$^{168}Er$
$Tc^{99}$
$Gd^{156}$
$Gd^{154}$
$Er^{167}$
$_{68}Er^{170}$
$Sm^{152}$
$Hf^{176}$
$Tm^{169}$
$U^{238}$
$Sm^{151}$
$Sm^{153}$
$_{62}Sm^{154}$
$Pr^{141}$
$Os^{186}$
$Os^{188}$
$Hf^{177}$
$Lu^{175}$
$Gd^{160}$
$Hf^{178}$
$Gd^{158}$
$Er^{166}$
$Cs^{133}$
$^{174}Yb$
$^{67}Zn$
$^{172}Yb$
$^{171}Yb$
$^{170}Yb$
$^{131}Xe$
$^{186}W$
$^{184}W$
$^{183}W$
$^{182}W$
$^{180}W$
$^{232}Th(^{228}Ra)$
$^{181}Ta$
$^{125}Te$
$^{147}Pm$
$^{149}Sm(^{145}Nd)$
$^{101}Ru$
$^{99}Ru$
$^{195}Pt$
$^{147}Pm(^{147}Sm)$
$^{189}Os$
$^{237}Np(^{233}Pa)$
$^{61}Ni$
$^{83}Kr$
$^{193}Ir$
$^{191}Ir$
$^{201}Hg$
$^{180}Hf$
$^{139}La$
$^{187}Re$
$^{234}U$
$^{236}U$
$^{239}Pu$
$^{190}Os$
$^{197}Au$
$^{133}Cs$

-continued

| | | | |
|---|---|---|---|
| $^{160}$Dy | | | |
| $^{166}$Er | | | |
| $^{155}$Gd | | | |
| $^{73}$Ge | | | |
| $^{178}$Hf | | | |
| K$^{40}$ | | | |
| Am$^{243}$ | | | |
| $^{145}$Nd | | | |
| $^{153}$Eu | | | |
| $^{129}$I($^{129}$Xe) | | | |
| $^{127}$I | | | |
| $^{119}$Sn | | | |
| $^{57}$Fe | | | |
| $^{151}$Eu | | | |
| $^{129}$Xe | | | |
| $^{164}$Dy | | | |
| $^{57}$Fe | | | |
| $^{161}$Dy | | | |
| $^{162}$Dy | | | |
| $^{117}$Sn | | | |
| $^{121}$Sb | | | |
| $^{127}$I | | | |
| $^{133}$Ba | | | |
| $^{145}$Nd | | | |
| $^{145}$Pm | | | |
| $^{147}$Sm | | | |
| $^{153}$Eu | | | |

23. The system of claim 22, wherein said tunable source includes an isotope selected from the following list:

| | | |
|---|---|---|
| $^{176}$Tm | | |
| $^{159}$Gd | $^{159}$Dy | |
| $^{165}$Dy | $^{165}$Yb | $^{165}$Er |
| $^{231}$Th | $^{231}$U | |
| $^{157}$Eu | $^{157}$Tb | |
| $^{164}$Ho | $^{164}$Tm | |
| $^{168}$Ho | $^{168}$Tm | |
| Mo$^{99}$ | | |
| Eu$^{156}$ | Tb$^{156}$ | |
| Eu$^{154}$ | Tb$^{154}$ | |
| Ho$^{167}$ | Tm$^{167}$ | |
| Ho$^{170}$ | Tm$^{170}$ | |
| Pm$^{152}$ | Eu$^{152m}$ | Eu$^{152}$ |
| Lu$^{176m}$ | Ta$^{176}$ | Lu$^{176}$ |
| Er$^{169}$ | Yb$^{169}$ | |
| Pu$^{242}$ | | |
| Pm$^{151}$ | | |
| Pm$^{153}$ | | |
| Pm$^{154}$ | Eu$^{154}$ | |
| Ce$^{141}$ | Nd$^{141}$ | |
| Re$^{186}$ | Ir$^{186}$ | |
| Re$^{188}$ | Ir$^{188}$ | |
| Lu$^{177m}$ | Ta$^{177}$ | Lu$^{177}$ |
| Yb$^{175}$ | Hf$^{175}$ | |
| Eu$^{160}$ | | |
| Lu$^{178}$ | Ta$^{178}$ | |
| Eu$^{158}$ | Tb$^{158}$ | |
| Ho$^{166m}$ | Tm$^{166}$ | Ho$^{166}$ |
| La$^{133}$ | Ba$^{133}$ | Xe$^{133}$ |
| $^{174m}$Tm | $^{174}$Lu | $^{174}$Tm |
| $^{67}$Cu | $^{67}$Ga | |
| $^{172}$Tm | $^{172}$Lu | |
| $^{171}$Tm | $^{171}$Lu | |
| $^{170}$Tm | $^{170}$Lu | |
| $^{131}$I | $^{131}$Cs | |
| $^{186}$Ta | $^{186}$Re | |
| $^{184}$Ta | $^{184m}$Re | $^{184}$Re |
| $^{183}$Ta | $^{183}$Re | |
| $^{182}$Ta | $^{182}$Re | |
| $^{180m}$Ta | $^{180}$Re | $^{180}$Ta |
| $^{236}$U | | |
| $^{236}$Pa | $^{240}$Pu | $^{236}$Np |
| $^{181}$Hf | $^{181}$W | |
| $^{125}$So | $^{125}$I | |
| $^{147}$Pm | $^{147}$Eu | |
| $^{149}$Pm | $^{149}$Eu | |
| $^{101}$Tc | $^{101m}$Rh | $^{101}$Rh |

-continued

| | | | |
|---|---|---|---|
| $^{99}$Tc | $^{99m}$Rh | $^{99}$Rh | |
| $^{195m}$Ir | $^{195}$Au | $^{195}$Ir | $^{195m}$Pt |
| $^{147}$Nd | | | |
| $^{189}$Re | $^{189}$Ir | | |
| $^{237}$U | $^{241}$Am | $^{237}$Pu | |
| $^{61}$Co | $^{61}$Cu | | |
| $^{83}$Br | $^{83}$Rb | $^{83m}$Kr | |
| $^{193}$Os | $^{193}$Pt | | |
| $^{191}$Os | $^{191}$Pt | | |
| $^{201}$Au | $^{201}$Tl | | |
| $^{180}$Lu | $^{180m}$Ta | $^{180}$Ta | |
| $^{139}$Ba | $^{139}$Ce | | |
| $^{187}$W | | | |
| $^{234m}$Pa | $^{238}$Pu | $^{234}$Np | $^{234}$Pa |
| $^{236}$Pa | $^{240}$Pu | $^{236}$Np | |
| $^{239}$Np | $^{243}$Cm | $^{239}$Am | |
| $^{190}$Re | $^{190}$Ir | | |
| $^{197}$Pt | $^{197}$Hg | | |
| $^{133}$Xe | $^{133}$Ba | | |
| $^{160}$Tb | $^{160}$Ho | | |
| $^{166m}$Ho | $^{166}$Tm | $^{166}$Ho | |
| $^{155}$Eu | $^{155}$Tb | | |
| $^{73}$Ga | $^{73}$As | | |
| $^{178}$Lu | $^{178}$Ta | | |
| Pu$^{243}$ | Bk$^{247}$ | | |
| $^{145}$Pr | $^{145}$Pm | | |
| $^{153}$Sm | $^{153}$Gd | | |
| $^{129m}$Te | | | |
| $^{127}$Te | $^{127}$Xe | | |
| $^{119m}$In | $^{119}$Sb | $^{119}$In | |
| $^{57}$Mn | $^{57}$Co | | |
| $^{151}$Sm | $^{151}$Gd | | |
| $^{129}$I | $^{129}$Cs | | |
| $^{164}$Tb | $^{164}$Ho | | |
| $^{57}$Mn | $^{57}$Co | | |
| $^{161}$Tb | $^{161}$Ho | | |
| $^{162}$Tb | $^{162}$Ho | | |
| $^{121m}$Sn | $^{121}$Sn | $^{121m}$Te | $^{121}$Te |
| $^{127}$Te | $^{127}$Xe | | |
| $^{129}$Te | $^{129m}$Te | | |
| $^{133}$La | | | |
| $^{145}$Pr | $^{145}$Pm | | |
| $^{147}$Pm | $^{147}$Eu | | |
| $^{153}$Sm | $^{153}$Gd | | |

24. The system of claim 22, wherein the tunable isotope and the absorber isotopes correspond as follows:

| Absorber | Source(s) | | | |
|---|---|---|---|---|
| $^{176}$Yb | $^{176}$Tm | | | |
| $^{159}$Tb | $^{159}$Gd | $^{159}$Dy | | |
| $^{165}$Ho | $^{165}$Dy | $^{165}$Yb | $^{165}$Er | |
| $^{231}$Pa | $^{231}$Th | $^{231}$U | | |
| $^{157}$Gd | $^{157}$Eu | $^{157}$Tb | | |
| $^{164}$Er | $^{164}$Ho | $^{164}$Tm | | |
| $^{168}$Er | $^{168}$Ho | $^{168}$Tm | | |
| Tc$^{99}$ | Mo$^{99}$ | | | |
| Gd$^{156}$ | Eu$^{156}$ | Tb$^{156}$ | | |
| Gd$^{154}$ | Eu$^{154}$ | Tb$^{154}$ | | |
| Er$^{167}$ | Ho$^{167}$ | Tm$^{167}$ | | |
| $_{68}$Er$^{170}$ | Ho$^{170}$ | Tm$^{170}$ | | |
| Sm$^{152}$ | Pm$^{152}$ | Eu$^{152m}$ | $^{152}$Eu | |
| Hf$^{176}$ | Lu$^{176m}$ | Ta$^{176}$ | Lu$^{176}$ | |
| Tm$^{169}$ | Er$^{169}$ | Yb$^{169}$ | | |
| U$^{238}$ | Pu$^{242}$ | | | |
| Sm$^{151}$ | Pm$^{151}$ | | | |
| Sm$^{153}$ | Pm$^{153}$ | | | |
| $_{62}$Sm$^{154}$ | Pm$^{154}$ | Eu$^{154}$ | | |
| Pr$^{141}$ | Ce$^{141}$ | Nd$^{141}$ | | |
| Os$^{186}$ | Re$^{186}$ | Ir$^{186}$ | | |
| Os$^{188}$ | Re$^{188}$ | Ir$^{188}$ | | |
| Hf$^{177}$ | Lu$^{177m}$ | Ta$^{177}$ | Lu$^{177}$ | |
| Lu$^{175}$ | Yb$^{175}$ | Hf$^{175}$ | | |
| Gd$^{160}$ | Eu$^{160}$ | | | |
| Hf$^{178}$ | Lu$^{178}$ | Ta$^{178}$ | | |
| Gd$^{158}$ | Eu$^{158}$ | Tb$^{158}$ | | |
| Er$^{166}$ | Ho$^{166m}$ | Tm$^{166}$ | Ho$^{166}$ | |
| Cs$^{133}$ | La$^{133}$ | Ba$^{133}$ | Xe$^{133}$ | |
| $^{174}$Yb | $^{174m}$Tm | $^{174}$Lu | $^{174}$Tm | |

-continued

| Absorber | Source(s) | | | |
|---|---|---|---|---|
| $^{67}Zn$ | $^{67}Cu$ | $^{67}Ga$ | | |
| $^{172}Yb$ | $^{172}Tm$ | $^{172}Lu$ | | |
| $^{171}Yb$ | $^{171}Tm$ | $^{171}Lu$ | | |
| $^{170}Yb$ | $^{170}Tm$ | $^{170}Lu$ | | |
| $^{131}Xe$ | $^{131}I$ | $^{131}Cs$ | | |
| $^{186}W$ | $^{186}Ta$ | $^{186}Re$ | | |
| $^{184}W$ | $^{184}Ta$ | $^{184m}Re$ | $^{184}Re$ | |
| $^{183}W$ | $^{183}Ta$ | $^{183}Re$ | | |
| $^{182}W$ | $^{182}Ta$ | $^{182}Re$ | | |
| $^{180}W$ | $^{180m}Ta$ | $^{180}Re$ | $^{180}Ta$ | |
| $^{232}Th(^{228}Ra)$ | $^{236}U$ | | | |
| $^{236}U$ | $^{236}Pa$ | $^{240}Pu$ | $^{236}Wp$ | |
| $^{181}Ta$ | $^{181}Hf$ | $^{181}W$ | | |
| $^{125}Te$ | $^{125}Sb$ | $^{125}I$ | | |
| $^{147}Pm$ | $^{147}Pm$ | $^{147}Eu$ | | |
| $^{149}Sm(^{145}Nd)$ | $^{149}Pm$ | $^{149}Eu$ | | |
| $^{101}Ru$ | $^{101}Tc$ | $^{101m}Rh$ | $^{101}Rh$ | |
| $^{99}Ru$ | $^{99}Tc$ | $^{99m}Rh$ | $^{99}Rh$ | |
| $^{195}Pt$ | $^{195m}Ir$ | $^{195}Au$ | $^{195}Ir$ | $^{195m}Pt$ |
| $^{147}Pm(^{147}Sm)$ | $^{147}Nd$ | | | |
| $^{189}Os$ | $^{189}Re$ | $^{189}Ir$ | | |
| $^{237}Np(^{233}Pa)$ | $^{237}U$ | $^{241}Am$ | $^{237}Pu$ | |
| $^{61}Ni$ | $^{61}Co$ | $^{61}Cu$ | | |
| $^{83}Kr$ | $^{83}Br$ | $^{83}Rb$ | $^{83m}Kr$ | |
| $^{193}Ir$ | $^{193}Os$ | $^{193}Pt$ | | |
| $^{191}Ir$ | $^{191}Os$ | $^{191}Pt$ | | |
| $^{201}Hg$ | $^{201}Au$ | $^{201}Ti$ | | |
| $^{180}Hf$ | $^{180}Lu$ | $^{180m}Ta$ | $^{180}Ta$ | |
| $^{139}La$ | $^{139}Ba$ | $^{139}Ce$ | | |
| $^{187}Re$ | $^{187}W$ | | | |
| $^{234}U$ | $^{234m}Pa$ | $^{238}Pu$ | $^{234}Np$ | $^{234}Pa$ |
| $^{236}U$ | $^{236}Pa$ | $^{240}Pu$ | $^{236}Np$ | |
| $^{239}Pu$ | $^{239}Np$ | $^{234}Cm$ | $^{239}Am$ | |
| $^{190}Os$ | $^{190}Re$ | $^{190}Ir$ | | |
| $^{197}Au$ | $^{197}Pt$ | $^{197}Hg$ | | |
| $^{133}Cs$ | $^{133}Xe$ | $^{133}Ba$ | | |
| $^{160}Dy$ | $^{160}Tb$ | $^{160}Ho$ | | |
| $^{166}Er$ | $^{166m}Ho$ | $^{166}Tm$ | $^{166}Ho$ | |
| $^{155}Gd$ | $^{155}Eu$ | $^{155}Tb$ | | |
| $^{73}Ge$ | $^{73}Ga$ | $^{73}As$ | | |
| $^{178}Hf$ | $^{178}Lu$ | $^{178}Ta$ | | |
| $K^{40}$ | none | | | |
| $Am^{243}$ | $Pu^{243}$ | $Bk^{247}$ | | |
| $^{145}Nd$ | $^{145}Pr$ | $^{145}Pm$ | | |
| $^{153}Eu$ | $^{153}Sm$ | $^{153}Gd$ | | |
| $^{129}I(^{129}Xe)$ | $^{129m}Te$ | $^{129}Te$ | | |
| $^{127}I$ | $^{127}Te$ | $^{127}Xe$ | | |
| $^{119}Sn$ | $^{119m}In$ | $^{119}Sb$ | $^{119}In$ | |
| $^{57}Fe$ | $^{57}Mn$ | $^{57}Co$ | | |
| $^{151}Eu$ | $^{151}Sm$ | $^{151}Gd$ | | |
| $^{129}Xe$ | $^{129}I$ | $^{129}Cs$ | | |
| $^{164}Dy$ | $^{164}Tb$ | $^{164}Ho$ | | |
| $^{57}Fe$ | $^{57}Mn$ | $^{57}Co$ | | |
| $^{161}Dy$ | $^{161}Tb$ | $^{161}Ho$ | | |
| $^{162}Dy$ | $^{162}Tb$ | $^{162}Ho$ | | |
| $^{117}Sn$ | | | | |
| $^{121}Sb$ | $^{121m}Sn$ | $^{121}Sn$ | $^{121m}Te$ | $^{121}Te$ |
| $^{127}I$ | $^{127}Te$ | $^{127}Xe$ | | |
| $^{129}I$ | $^{129}Te$ | $^{129m}Te$ | | |
| $^{133}Ba$ | $^{133}La$ | | | |
| $^{145}Nd$ | $^{145}Pr$ | $^{145}Pm$ | | |
| $^{145}Pm$ | | | | |
| $^{147}Sm$ | $^{147}Pm$ | $^{147}Eu$ | | |
| $^{153}Eu$ | $^{153}Sm$ | $^{153}Gd$ | | |

25. Apparatus for therapeutic administration of radiation for selective necrosis of target tissue, comprising
a source of radiation selectively providing at least one frequency of radiation emission;
means for tuning the frequency of said source radiation;
filter means for selective transmittance of said radiation emission of said source of radiation providing filtered radiation emission proximally disposed to said target tissue; and
means for selective absorption of said filtered radiation emission;
means for providing a magnetic field on said target tissue to produce a shifted Mossbauer absorption frequency of said means for selective absorption; and
means for applying said filtered radiation emission to said means for selective absorption, wherein
said source is adjusted to provide sufficient filtered radiation at the frequency corresponding to the shifted Mossbauer frequency of said means for selective absorption at the target tissue to provide necrosis.

26. The apparatus of claim 25, wherein
said means for tuning comprises Doppler shift means.

27. The apparatus of claim 25, wherein
said filter means comprises crystal diffraction means.

28. The apparatus of claim 25, wherein
the excited component of said target tissue emits radiation causing necrosis of said target tissue, the apparatus further comprising
means for detecting said target tissue radiation.

29. The apparatus of claim 25, further comprising
means for sensing target tissue filtered radiation fluorescence along a path off-axis from the incident radiation providing a corresponding sensed fluorescence output signal.

30. The apparatus of claim 28, further comprising
means for imaging said target tissue according to said target tissue radiation.

31. The apparatus of claim 25, wherein
said means for selective absorption comprises at least one of a molecule, a protein, and a peptide, wherein said means for selective absorption further includes naturally occurring and synthesized elements.

32. The apparatus of claim 31, wherein
said means for selective absorption comprises at least one of an isotope and a hormone.

33. The apparatus of claim 32, wherein
said means for selective absorption is administered as a pharmaceutical.

34. Apparatus for therapeutic administration of radiation for selective necrosis of target tissue, comprising
a source of radiation selectively providing at least one frequency of radiation emission;
filter means for selective transmittance of said radiation emission providing a filtered radiation emission;
means for selective absorption of said filtered radiation emission proximally disposed to said target tissue;
means for providing a magnetic field at said target tissue to produce a shifted Mossbauer absorption frequency of said means for selective absorption; and
means for applying said filtered radiation emission to said target tissue, wherein
said magnetic field is adjusted to provide a shifted Mossbauer frequency of the means for selective absorption which coincides with the frequency of the filtered radiation emission to provide necrosis.

35. Apparatus for selective therapy comprising:
means for absorbing Mossbauer excitation emission having a nuclei located at a target tissue;
means for polarizing the nuclei of the means for absorbing; and
means for producing an excitation emission corresponding to a Mossbauer absorption energy level of said means for absorbing Mossbauer excitation emission at the selected polarization causing cell damage at said target tissue.

36. The apparatus of claim 35, wherein said means for polarizing the nuclei comprises means for applying a directed magnetic field thereon.

37. The apparatus of claim 36, wherein said means providing a directed magnetic field includes a plurality of Helmholtz coils.

38. The apparatus of claim 35, wherein said means for causing selective absorption comprises $^{57}$Fe Bleomycin.

* * * * *